United States Patent [19]

Panster et al.

[11] Patent Number: 4,584,395
[45] Date of Patent: Apr. 22, 1986

[54] METHOD FOR PREPARATION OF 3-CHLOROPROPYL-TRICHLOROSILANE

[75] Inventors: Peter Panster, Rodenbach; Rudolf Michel, Freigericht, both of Fed. Rep. of Germany; Wolfgang Buder, Salvador, Brazil; Peter Kleinschmit, Hanau, Fed. Rep. of Germany

[73] Assignee: Degussa Aktiengesellschaft, Frankfurt, Fed. Rep. of Germany

[21] Appl. No.: 699,696

[22] Filed: Feb. 8, 1985

[30] Foreign Application Priority Data

Feb. 10, 1984 [DE] Fed. Rep. of Germany ....... 3404703

[51] Int. Cl.$^4$ ............................................... C07F 7/08
[52] U.S. Cl. .................................................. 556/479
[58] Field of Search ....................................... 556/479

[56] References Cited

U.S. PATENT DOCUMENTS

| | | | |
|---|---|---|---|
| 3,419,593 | 12/1968 | Willing | 556/479 |
| 3,715,334 | 2/1973 | Karstedt | 556/479 X |
| 3,814,730 | 6/1974 | Karstedt | 556/479 X |
| 4,292,433 | 9/1981 | Koga et al. | 556/479 |
| 4,398,010 | 8/1983 | Adkins | 556/479 X |
| 4,503,160 | 3/1985 | Williams | 556/479 X |

Primary Examiner—Paul F. Shaver
Attorney, Agent, or Firm—Beverige, DeGrandi & Weilacher

[57] ABSTRACT

A method for the preparation of 3-chloropropyltrichlorosilane is carried out by conversion of trichlorosilane with allylchloride in the presence of a platinum containing polymeric organosiloxane-ammonium compound containing units represented by the structural formula:

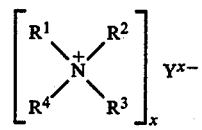

(1)

wherein $R^1$, $R^2$ and $R^3$ represent a group of the formula:

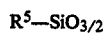

(2)

wherein $R^5$ denotes an alkylene group and the free valences of the oxygen atoms are saturated by silicon atoms of further groups of the formula (2), optionally with incorporation of crosslinking agents, $R^4$ has the same meaning as $R^1$, $R^2$ and $R^3$ or hydrogen, alkyl, cycloalkyl or benzyl, $Y^{x-}$ represents $PtX_4^{2-}$ or $PtX_6^{2-}$ (X is Cl or Br) and can also be an inorganic 1 to 3 functional anion of a protonic acid which yields stable salts with amine bases or the hydroxy group, and x is a number from 1 to 3.

11 Claims, No Drawings

METHOD FOR PREPARATION OF 3-CHLOROPROPYL-TRICHLOROSILANE

The invention pertains to a method for the preparation of 3-chloropropyl-trichlorosilane wherein this important intermediate product may be obtained in a high yield by introduction of comparatively limited excess of trichlorosilane and under substantially reduced production of undesired silicon containing side products. The method according to the present invention includes the introduction of new hydrosilylation catalysts which are further described in the related application filed simultaneously herewith and identified by the German priority application No. P 34 04 702.6-44 corresponding to U.S. application Ser. No. 699,968 filed Feb. 8, 1985 which under the chosen reaction conditions bring about a selected hydrosilylation of allylic double bonds and with that enables the advantageous production of the desired products.

3-chloropropyl-trichlorosilane is an important technical intermediate in organosilane chemistry. By the esterification of the Si—Cl-functional groups with alcohols and optionally through substitution reactions on the C—Cl-moiety, it is possible to prepare from these compounds further important organosilanes, such as for example bis(3-triethoxysilylpropyl)tetrasulfane, which can be introduced predominantly as an adhesive aid between inorganic and organic polymer systems.

According to the conventional technical methods, the preparation of 3-chloropropyl-trichlorosilane is carried out through the addition of trichlorosilane with allylchloride in the presence of hydrosilylation catalysts formed of elementary platinum which are deposited on a carbon carrier (U.S. Pat. No. 2,637,738 and German Pat. Nos. 20 12 229 and 28 15 316) or as a soluble platinum compound in the most simple state, for example, $H_2PtCl_6 \times 6H_2O$ (see German OS No. 28 51 456; CS-PS No. 187 167; U.S. Pat. No. 4,292,433; U.S. Pat. No. 4,292,434; DE-AS No. 11 87 240 and DE-PS No. 11 65 028).

While the heterogeneous catalyst systems used in commercial applications have the advantages of easy separability and ability to be recycled, and which permit the valuable platinum to be easily recovered, the homogeneous platinum catalysts that are used are somewhat more active and are also somewhat more selective and are more reproducible. The separation of these out of the reaction medium and the recovery of the platinum is however costly and problematical. All catalysts used for hydrosilylation which up to now have been introduced for the addition reaction of trichlorosilane with allylchloride, in general however also produce, in addition to the desired product 3-chloropropyl-trichlorosilane, considerable amounts of the undesired side product propyltrichlorosilane. This is because in addition to the hydrosilylation reaction which proceeds according to the equation:

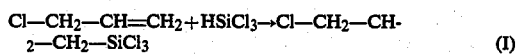

there also occurs a reduction of the allylchloride to propene with a portion of 25 to 30 mol percent, according to the equation II:

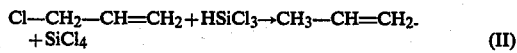

By reason of the reduced selectivity of the heretofore used catalysts for hydrosilylation with regard to the hydrosilylation of allylic double bonds, the formed propene reacts immediately in concurrence with the aforenamed trichlorosilane with allylchloride to form propyltrichloro-silane according to the equation III:

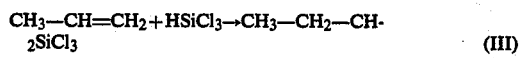

As a consequence of this restricted selectivity, in order to achieve a complete reaction of the introduced allylchloride, there is always, a definite excess of at least 25 to 30 mol percent trichlorosilane necessary and there is also obtained besides the still utilizable silicon tetrachloride, the compound propyltrichlorosilane, which frequently cannot be utilized or is only difficult to utilize.

It therefore was desirable to find a new hydrosilylation method according to which the desired product 3-chloropropyl-trichlorosilane can be obtained in high yields with the introduction of only a slight excess of trichlorosilane and with a strong limitation on the formation of the undesired side product propyltrichlorosilane as well as only a limited production of silicon tetrachloride.

This method is characterized by the fact that the trichlorosilane and allylchloride are reacted with each other in the presence of a platinum containing polymeric organosiloxane-ammonium compound which is formed of units of the general formula:

wherein $R^1$, $R^2$ and $R^3$ represent a group of the general formula (2); namely:

wherein $R^5$ stands for a linear or branched alkylene group having 1 to 12 carbon atoms, a cycloalkylene group having 5, 7 or 8 carbon atoms or entities of the formula:

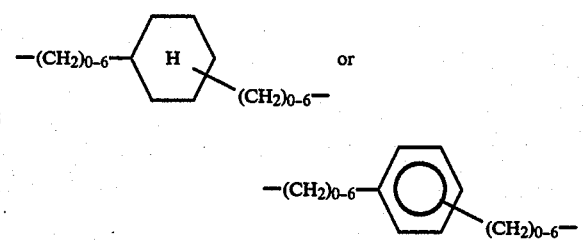

$R^1$, $R^2$ and $R^3$ are the same or different and the free valences of the oxygen atom are satisfied either by silicon atoms or additional groups of the formula (2) and/or through crosslinking bridging units of the formula:

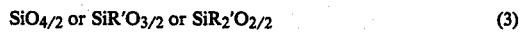

wherein

R' is either methyl or ethyl and the ratio between the silicon atom in the formula (2) and the silicon atom of the bridging groups according to formula (3) ranges from 1:1 and 1:10, $R^4$ can have the same scope of meaning as defined by $R^1$, $R^2$ and $R^3$, or stands for hydrogen, a 1 to 10 carbon atom containing linear or branched alkyl group, a 5 to 8 carbon atom containing cycloalkyl or benzyl group, $Y^{x-}$ stands for:

$PtCl_4^{2-}$ or $PtCl_6^{2-}$ $PtBr_4^{2-}$ or $PtBr_6^{2-}$ and for an inorganic 1 to 3 valent anion of an inorganic protonic acid which is able to form stable salts with amine base, or for the hydroxy group, and x is a number from 1 to 3.

In this polymer formation, there can be used a variety of units according to formula (1) next to each other if this is advantageous with regard to the catalytic properties.

Typical examples for inorganic 1 to 3 valent anions which can be present in addition to the complex anions of the platinum in the polymeric organosiloxane-ammonium compounds are chloride, bromide, iodide, sulfate, nitrate, phosphate or carbonate. The molar ratio between the complex anions of the platinum and the inorganic anions such as hydroxide can range from 1:0 to 1:50, however from the viewpoint of obtaining as high as possible an activity and selectivity it is preferable that the relationship be 1:0 to 1:10.

The introduction of the silicon containing crosslinking agents serves to control the platinum density in the solid material as well as to control the specific surface area, with an additional influence on the activity and selectivity of the catalyst.

According to an advantageous embodiment of the invention, the catalyst is selected according to formula (1) wherein $R^1$, $R^2$ and $R^3$ are each identical with other and $R^4$ is methyl.

Particular advantages with respect to the selection of the raw materials and the material properties of the catalysts used in accordance with the method of the present invention reside in compounds that are created as a result of the polymeric units having the formula:

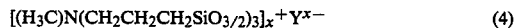

$$[(H_3C)N(CH_2CH_2CH_2SiO_{3/2})_3]_x^+ Y^{x-} \qquad (4)$$

wherein $Y^{x-}$ represents $PtCl_4^{2-}$ or chloride, and the free valences of the oxygen atom attached to the silicon atom are either saturated by silicon atoms of additional groups of the formula (4) and/or by crosslinking bridging groups having the formula $SiO_{4/2}$, wherein the relationship between the silicon atoms in formula (4) and the silicon atoms of the bridging group $SiO_{4/2}$ ranges from 1:0.1 to 1:10.

The platinum concentration in the solid material can range theoretically from less than a part per million up to over 20 weight percent; for the practical application of the present invention, however, the platinum content is preferably 2 to 20 weight percent.

Although the selected hydrosilylation catalysts according to formula (1) can be used in principle also as solid bed contact catalysts, for example, in a loop reactor, the method of the present invention permits utilization thereof with particular advantage as a suspension catalyst. In this way, the catalyst is introduced into an agitated liquid phase of the mixture of the reaction components, composed essentially of chloropropyl-trichlorosilane, silicon tetrachloride and small amounts of propyltrichlorosilane and/or the starting raw materials trichlorosilane and allylchloride. This method of proceeding in accordance with the invention is advantageous because the catalyst can be used in relatively finely divided form and as a result diffusion problems are avoided which as a result benefits the catalyst activity. In addition, the application as a suspension catalyst favors the already inherent high selectivity, of the catalysts to be used in accordance with the inventive process for hydrolsilylation in a manner such that in the simultaneously running side reaction, the propene that is formed can escape immediately after its formation removed from the solution and because of the short dwell time in solution, it has insufficient time to react with simultaneously present trichlorosilane to produce the undesired side product propyltrichlorosilane. The utilization of an excess pressure over atmospheric pressure is therefore not necessary although excess pressure, because of the higher selectivity of the utilized catalyst, is applicable in principle.

The method of the present invention can in principle be carried out continuously or discontinuously without substantial influence on the formation of the product. In regard to a rational technical practicable embodiment of the invention with large throughputs of material, it is, of course, most suitable for the process steps to be carried out in a continuous manner. However in a continuous process, one must be cognizant of the fact that for a quantitative conversion of the raw materials trichlorosilane and allylchloride to the desired product 3-chloropropyl-trichlorosilane, a sufficient dwell time must be applied.

In the practice of the invention, the continuously operating process of the invention can be carried out in the most simple manner by introducing the catalyst into the reaction mixture of the previously described reaction components and agitating according to conventional techniques, for example, through stirring. Both raw materials are each independently added or previously mixed together and then added to this mixture. Parallel to the introduction of the reactants, the product mixture is withdrawn from the reactor at a specific area of the reactor, possibly under intermediate connection of an apparatus for separation of the catalyst. The freed propene is then permitted to be removed by means of a cooler, which is preferably cooled with a cooling brine at a temperature of less than 0° C.; it can then be conveyed to a further utilization.

With regard to obtaining the highest throughput, it is advantageous to carry out the conversion of the trichlorosilane and allylchloride into 3-chloropropyl-trichlorosilane at elevated temperature, especially at the reflux temperature of the reaction mixture; that is, between about 70° to 130° C. A high reflux temperature of the reaction mixture is characteristic of a high catalyst selectivity and a high degree of conversion, provided that no reaction component is introduced in a greater excess.

In order to obtain a complete reaction of the allylchloride, it is also necessary in the process of the present invention to have a slight excess of the trichlorosilane. This necessary excess amounts to 5 to 20 mol percent and at that is considerably lower than is the case in conventional procedures which have heretofore been utilized.

The use of the catalyst as a suspension catalyst in the continuously operating process as compared to its use as a solid bed catalyst, has the additional advantage, that a partial removal of the used catalyst and the introduction of fresh catalysts can be carried out without interruption of the process.

This advantageous application of a suspension is only possible by using the catalysts to be applied in the process of the present invention becuse only these catalysts possess the necessary abrasion resistance to enable operation without disturbance and only in this case there is such a high concentration of platinum that the catalytically active solid material portion in the suspension can be held relatively low and even in spite of that, obtain a high throughput. The utilization of a conventional hydrosilylation catalyst with a concentration of a maximum of 1 to 2% platinum on charcoal as a suspension catalyst is only possible in a technical scale to a low degree because of the high abrasion of the charcoal and the loss of platinum resulting therefrom and because of the necessary high solid material concentration in the reaction medium. The conventional utilization of those solid bed catalysts does not in any way support the not very high selectively of these conventional catalysts so that the propene which is set free in the reaction is almost completely reacted to the undesired side product propyltrichlorosilane.

The invention will be illustrated in the following representative examples with regard to the generally most important catalyst types.

EXAMPLE 1

In a 2 liter four neck flask equipped with an interior thermometer, a KPG-stirrer, liquid introduction means, a port provided with a fritted closure for removal of the liquid and an intensive reflux cooler which is cooled with a cooling brine at $-25°$ C. and which is provided at the upper end with a gas vent, is filled with 1.5 liter 3-chloropropyl-trichlorosilane and 37.4 g of a hydrosilylation catalyst. The latter is formed from a platinum containing polymeric organosiloxane-ammonium compound having units of the formula:

and units of the formula:

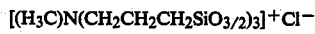

with a platinum content of 10.7 weight percent and a particle size of 0.05 to 0.2 mm. By providing heating with a heater (Heizpilz), the temperature of the mixture was brought up to about 100° C. and the velocity of the stirring of the KPG-stirrer was set at about 60 rpm.

With the help of a dosing pump, there is pumped out of a stock vessel at an hourly rate of 200 ml per hour a mixture of allylchloride and trichlorosilane which has a molar ratio of 1.0:1.1 and which was introduced into the reaction flask. At the same time, on a opposite side of the vessel, the product mixture was removed through a port containing the built in frit which retains the catalyst. The propene formed in the reaction can be taken out of reaction system at the head of the intensive cooler and conveyed to a scrubber that is filled with a white oil and then to a gas burette and from there is released through a wash flask which is filled with 2n-NaOH. In the course of the equilibration which follows, the temperature in the reactor was then so regulated that the mixture easily boiled. After 30 hours of reaction time, the boiling temperature was 106° C. and over a time period of about 3 hours a sample was taken accurately: the throughput of product mixture amounted to 205 g per hour and the propene formed in an amount of about 0.17 mol per hour. According to a gas chromatographic determination, the product mixture had the following composition:

2.6 weight percent trichlorosilane
0.3 weight percent allylchloride
17.6 weight percent SiCl$_4$
3.8 weight percent propyltrichlorosilane
74.5 weight percent chloropropyltrichlorosilane
1.2 weight percent miscellaneous components Therefore, the basic selectivity of the introduced catalyst permits the production of the desired product 3-chloropropyl-trichlorosilane to the extent of 77.2%. This value expresses therewith also approximately the yield of chloropropyltrichlorosilane, based on the allylchloride that was introduced. The propene formed as a result of the side reactions could, as determined by analysis, escape to about 80% from the reaction mixture.

After 80 hours of reaction time, there was carried through an experiment with the same hourly rate. This time the product mixture had the following composition:

2.5 weight percent trichlorosilane
0.2 weight percent allylchloride
18.3 weight percent SiCl$_4$
3.6 weight percent propyltrichlorosilane
73.8 weight percent chloropropyltrichlorosilane
1.6 weight percent miscellaneous components The selectivity for 3-chloropropyl-trichlorosilane amounted to 76.4%. The propene that was formed in the side reaction was determined to be about 81% of the reaction mixture. The catalyst utilized showed no distinct evidence of abrasion even after this time.

In a comparative example, a conventional platinum/-charcoal hydrolsilylation catalyst was utilized under analogous reaction conditions as were utilized with the aforementioned catalyst of the invention. After the equilibrium was established, there was obtained a GC-analysis of the product mixture according to the following:

0.0 weight percent trichlorosilane
1.2 weight percent allylchloride
18.1 weight percent SiCl$_4$
12.5 weight percent propyltrichlorosilane
63.6 weight percent chloropropyltrichlorosilane
4.6 weight percent miscellaneous components The selectivity for 3-chloropropyl-trichlorosilane amounted in this case only to 73.8%. Only 34% of the formed propene could be removed from the reaction mixture and this only because there was no further trichlorosilane to go through to the hydrosilylation reaction. Also, a considerably higher percentage of the raw material allylchloride remained unreacted in the product mixture and the catalyst abrasion was after a time so great that in this case, no commercial long term run would be possible.

EXAMPLE 2

With analogous reaction conditions as described in Example 1, a series of additional platinum containing organopolysiloxane-ammonium compounds were used as catalysts for the trichlorosilane-addition to allylchloride. The results obtained are set forth in the following tables:

| | Polymer Units in Catalyst | Pt Wt % | Amount (g) | Mol-ratio allylchloride HSiCl$_3$ | Yield throughput product mixture g/h |
|---|---|---|---|---|---|
| Example 2 | [(H$_3$C)N(CH$_2$CH$_2$CH$_2$SiO$_{3/2}$)$_3$]$_2^{2+}$PtCl$_4^{2-}$.SiO$_2$ + (H$_3$C)N(CH$_2$CH$_2$CH$_2$SiO$_{3/2}$)$_3^+$Cl$^-$ | 9.72 | 21.88 | 1:1.05 | 167 |
| Example 3 | {(H$_3$C)$_2$CH—CH$_2$—N[(CH$_2$)$_8$SiO$_{3/2}$]$_3$}$_2^{2+}$PtCl$_6^{2-}$ + {(H$_3$C)$_2$CH—CH$_2$—N[(CH$_2$)$_8$SiO$_{3/2}$]$_3$}$_2^{2+}$SO$_4^{2-}$ | 1.52 | 28.5 | 1:1.1 | 52 |
| Example 4 | [N(CH$_2$CH$_2$CH$_2$SiO$_{3/2}$)$_4$]$_2^{2+}$PtCl$_4^{2-}$ + [N(CH$_2$CH$_2$CH$_2$SiO$_{3/2}$)$_4$]$^+$Cl$^-$ | 4.25 | 23.53 | 1:1.2 | 60 |
| Example 5 | [(H$_3$C)N(CH$_2$CH$_2$CH$_2$SiO$_{3/2}$)(CH$_2$—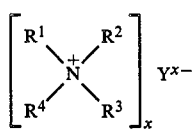—SiO$_{3/2}$)$_2$]$_2^{2+}$PtCl$_4^{2-}$.3(C$_2$H$_5$)$_2$SiO | 10.5 | 9.52 | 1:1.1 | 96 |
| Example 6 | [HN(CH$_2$CH$_2$CH$_2$SiO$_{3/2}$)$_3$]$_2^{2+}$PtCl$_6^{2-}$.2SiO$_2$ + N(CH$_2$CH$_2$CH$_2$SiO$_{3/2}$)$_3$.SiO$_2$ | 9.3 | 21.51 | 1:1.1 | 220 |
| Example 7 | {(H$_3$C)N[(CH$_2$)$_{10}$SiO$_{3/2}$]$_3$}$_2^{2+}$PtBr$_4^{2-}$ | 11.2 | 17.7 | 1:1.15 | 80 |

| | Product Mixture Composition | | | | | | | |
|---|---|---|---|---|---|---|---|---|
| | HSiCl$_3$ (wt %) | C$_3$H$_5$Cl (wt %) | SiCl$_4$ (wt %) | C$_3$H$_7$SiCl$_3$ (wt %) | Cl—C$_3$H$_6$—SiCl$_3$ (wt %) | Miscel. (wt %) | Selectivity* (%) | Propene yield** (%) |
| Example 2 | — | — | 19.5 | 6.3 | 74.0 | 0.2 | 75.3 | 69 |
| Example 3 | 3.1 | 0.2 | 18.0 | 3.7 | 74.2 | 0.8 | 76.8 | 80 |
| Example 4 | 4.9 | 0.3 | 16.9 | 2.9 | 73.7 | 1.3 | 77.8 | 84 |
| Example 5 | 2.8 | 0.1 | 18.1 | 3.2 | 74.8 | 1.0 | 76.8 | 83 |
| Example 6 | 2.9 | — | 17.0 | 4.6 | 74.6 | 0.9 | 77.9 | 74 |
| Example 7 | 3.8 | 0.2 | 19.2 | 2.6 | 73.8 | 0.4 | 75.5 | 87 |

*Selectivity for production of chloropropyltrichlorosilane
**Portion of released propene from the total intermediately formed propene Further variations and modifications of the present invention will be apparent to those skilled in the art from a study of the foregoing description of the invention and are intended to be encompassed by the claims appended hereto.

The entire disclosure of the German patent application No. P 34 04 703.4 is relied on and incorporated herein by reference.

We claim:

1. A method for the preparation of 3-chloropropyltrichlorosilane comprising reacting trichlorosilane and allylchloride together in the presence of a platinum containing polymeric organosiloxane-ammonium compound containing units represented by the formula:

  (1)

wherein R$^1$, R$^2$ and R$^3$ represent a group of the formula:

$$R^5\text{—SiO}_{3/2} \qquad (2)$$

wherein R$^5$ is linear or branched chain alkylene having 1 to 12 carbon atoms, cycloalkylene having 5, 7 or 8 carbon atoms or a moitey having the formula:

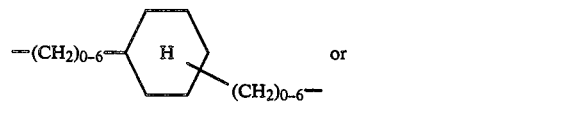

or

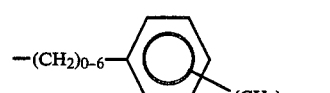

wherein R$^1$, R$^2$ and R$^3$ are the same or different and the free valences of the oxygen atoms are saturated by silicon atoms or further groups of the formula (2) and/or by crosslinking bridging agents having the formula:

$$\text{SiO}_{4/2} \text{ or SiR'O}_{3/2} \text{ or SiR}_2'\text{O}_{2/2} \qquad (3)$$

wherein
R' represents methyl or ethyl
and the ratio between the silicon atom and formula (2) and the silicon atom in the bridging units according to formula (3) is from 1:0 to 1:10
R$^4$ has the same scope of meaning as R$^1$, R$^2$ and R$^3$, or hydrogen, a 1 to 10 carbon atom containing linear or crosslinked alkyl, a 5 to 8 carbon atom containing cycloalkyl or benzyl,
Y$^{x-}$ is:

PtCl$_4^{2-}$ or PtCl$_6^{2-}$

PtBr$_4^{2-}$ or PtBr$_6^{2-}$ and represents an inorganic 1 to 3 valent anion of an inorganic protonic acid which will form stable salts with an amine base, or the hydroxy group and x is a number from 1 to 3.

2. The method for the preparation of 3-chloropropyltrichlorosilane according to claim 1 further comprising that the molecular ratio between the complex anion of the platinum and the inorganic anion of a protonic acid or hydroxy group is 1:0 to 1:10.

3. The method according to claim 1 further comprising wherein R$^1$, R$^2$ and R$^3$ are each identical and R$^4$ is methyl.

4. The method according to claim 1 further comprising reacting the trichlorosilane and allylchloride together in the presence of a platinum containing organosiloxane-ammonium compound which contains units represented by the formula:

[(H$_3$C)N(CH$_2$CH$_2$CH$_2$SiO$_{3/2}$)$_3$]$_x^+$Y$^{x-}$  (4)

wherein $Y^{x-}$ is $PtCl_4{}^{2-}$ and chloride, the free valences of the oxygen atoms are saturated by either silicon atoms or groups of the formula (2) and/or by crosslinking bridging agents of the formula $SiO_{4/2}$ wherein the ratio between the Si-atoms in (4) to the Si-atoms in the bridging agents $SiO_{4/2}$ ranges from 1:0.1 to 1:10.

5. The method according to claim 1 further comprising wherein the platinum content of the polymeric organosiloxane-ammonium compound ranges from 2 to 20 weight percent.

6. The method according to claim 1 further comprising the polymeric platinum containing organosiloxane-ammonium compound is introduced as a suspension catalyst.

7. The method according to claim 1 further comprising wherein the conversion of the trichlorosilane with the allylchloride is carried out at normal pressure and removing the propene which is formed as a result of the side reaction by escape from the reaction suspension through a cooler.

8. The method according to claim 1 further comprising carrying out the reaction in a continuous manner.

9. The method according to claim 1 further comprising reacting the trichlorosilane and allylchloride in a temperature range of 70° to 130° C.

10. The method according to claim 1 further comprising using trichlorosilane in an excess of 5 to 20 mol percent based on the allylchloride.

11. The method according to claim 1 wherein the polymeric platinum containing organosiloxane ammonium compound is solid and is present in the form of a suspension in an agitated liquid phase comprising trichlorosilane and allylchloride, removing the propene which is formed in the reaction between the said silane and allylchloride and withdrawing the product.

* * * * *